(12) United States Patent
Yoshida et al.

(10) Patent No.: US 10,745,448 B2
(45) Date of Patent: Aug. 18, 2020

(54) ANTIVIRAL PEPTIDE AND USE THEREFOR

(71) Applicants: TOAGOSEI CO., LTD., Tokyo (JP); NATIONAL UNIVERSITY CORPORATION HOKKAIDO UNIVERSITY, Hokkaido (JP)

(72) Inventors: Tetsuhiko Yoshida, Ibaraki (JP); Ayato Takada, Hokkaido (JP); Nahoko Baileykobayashi, Ibaraki (JP)

(73) Assignee: Toagosei Co., LTD, Tokyo (JP)

( * ) Notice: Subject to any disclaimer, the term of this patent is extended or adjusted under 35 U.S.C. 154(b) by 7 days.

(21) Appl. No.: 16/149,435

(22) Filed: Oct. 2, 2018

(65) Prior Publication Data

US 2019/0100562 A1 Apr. 4, 2019

(30) Foreign Application Priority Data

Oct. 3, 2017 (JP) ................. 2017-193292

(51) Int. Cl.
*C07K 14/11* (2006.01)
*A61P 31/16* (2006.01)
*C07K 14/005* (2006.01)
*C07K 14/145* (2006.01)
*C07K 14/00* (2006.01)

(52) U.S. Cl.
CPC .............. *C07K 14/11* (2013.01); *A61P 31/16* (2018.01); *C07K 14/001* (2013.01); *C07K 14/005* (2013.01); *C07K 14/145* (2013.01); *C07K 2319/02* (2013.01); *C07K 2319/10* (2013.01); *C12N 2760/16122* (2013.01); *C12N 2760/16222* (2013.01); *C12N 2760/20222* (2013.01)

(58) Field of Classification Search
None
See application file for complete search history.

(56) References Cited

U.S. PATENT DOCUMENTS

2009/0012000 A1 1/2009 Yoshida et al.
2009/0258815 A1 10/2009 Yoshida et al.

FOREIGN PATENT DOCUMENTS

| JP | 2007-230903 | 9/2007 |
|---|---|---|
| JP | 2007-230904 | 9/2007 |
| WO | WO2009/019612 | 2/2009 |
| WO | WO2011/151341 | 12/2011 |
| WO | WO 2016/189326 A1 * | 12/2016 |

OTHER PUBLICATIONS

Kobayashi et al., Protein & Peptide Letters, 2010, 17:1480-1488. (Year: 2010).*

* cited by examiner

*Primary Examiner* — Stacy B Chen
(74) *Attorney, Agent, or Firm* — Occhiuti & Rohlicek LLP

(57) ABSTRACT

An antiviral peptide provided by the present invention includes:
(1) the signal sequence of a glycoprotein encoded for by the G gene of the vesicular stomatitis virus (VSV), or the signal sequence of hemagglutinin encoded for by the HA gene of the influenza A or influenza B virus, or a modified amino acid sequence formed by conservative substitution of 1, 2 or 3 amino acid residues in any of these signal sequences; and
(2) an amino acid sequence that functions as a cell penetrating peptide (CPP).

5 Claims, No Drawings

Specification includes a Sequence Listing.

SEQUENCE LISTING

```
<160> NUMBER OF SEQ ID NOS: 28

<210> SEQ ID NO 1
<211> LENGTH: 16
<212> TYPE: PRT
<213> ORGANISM: Vesicular stomatitis virus

<400> SEQUENCE: 1

Met Leu Ser Tyr Leu Ile Phe Ala Leu Ala Val Ser Pro Ile Leu Gly
1               5                   10                  15

<210> SEQ ID NO 2
<211> LENGTH: 16
<212> TYPE: PRT
<213> ORGANISM: Influenza A virus

<400> SEQUENCE: 2

Met Lys Thr Ile Ile Ala Leu Ser Tyr Ile Phe Cys Leu Ala Leu Gly
1               5                   10                  15

<210> SEQ ID NO 3
<211> LENGTH: 15
<212> TYPE: PRT
<213> ORGANISM: Influenza B virus

<400> SEQUENCE: 3

Met Lys Ala Ile Ile Val Leu Leu Met Val Val Thr Ser Asn Ala
1               5                   10                  15

<210> SEQ ID NO 4
<211> LENGTH: 16
<212> TYPE: PRT
<213> ORGANISM: Vesicular stomatitis virus

<400> SEQUENCE: 4

Met Lys Cys Leu Leu Tyr Leu Ala Phe Leu Phe Ile Gly Val Asn Cys
1               5                   10                  15

<210> SEQ ID NO 5
<211> LENGTH: 16
<212> TYPE: PRT
<213> ORGANISM: Influenza A virus

<400> SEQUENCE: 5
```

Met Lys Thr Ile Ile Ala Leu Ser Tyr Ile Phe Cys Gln Val Leu Ala
1               5                   10                  15

<210> SEQ ID NO 6
<211> LENGTH: 16
<212> TYPE: PRT
<213> ORGANISM: Influenza A virus

<400> SEQUENCE: 6

Met Lys Thr Ile Ile Ala Leu Ser Tyr Ile Phe Cys Leu Val Phe Ala
1               5                   10                  15

<210> SEQ ID NO 7
<211> LENGTH: 16
<212> TYPE: PRT
<213> ORGANISM: Influenza A virus

<400> SEQUENCE: 7

Met Lys Thr Ile Ile Ala Leu Ser Tyr Ile Phe Cys Leu Val Leu Gly
1               5                   10                  15

<210> SEQ ID NO 8
<211> LENGTH: 14
<212> TYPE: PRT
<213> ORGANISM: Artificial sequence
<220> FEATURE:
<223> OTHER INFORMATION: Synthetic peptide

<400> SEQUENCE: 8

Arg Ser Arg Lys Tyr Thr Ser Trp Tyr Val Ala Leu Lys Arg
1               5                   10

<210> SEQ ID NO 9
<211> LENGTH: 19
<212> TYPE: PRT
<213> ORGANISM: Artificial sequence
<220> FEATURE:
<223> OTHER INFORMATION: Synthetic peptide

<400> SEQUENCE: 9

Met Ala Lys Ser Ile Arg Ser Lys His Arg Arg Gln Met Arg Met Met
1               5                   10                  15

Lys Arg Glu

<210> SEQ ID NO 10
<211> LENGTH: 16
<212> TYPE: PRT
<213> ORGANISM: Artificial sequence
<220> FEATURE:
<223> OTHER INFORMATION: Synthetic peptide

<400> SEQUENCE: 10

Met Ala Arg Arg Arg Arg His Arg Gly Pro Arg Arg Pro Arg Pro Pro
1               5                   10                  15

<210> SEQ ID NO 11
<211> LENGTH: 19
<212> TYPE: PRT
<213> ORGANISM: Artificial sequence
<220> FEATURE:
<223> OTHER INFORMATION: Synthetic peptide

<400> SEQUENCE: 11

Gly Arg Cys Arg Arg Leu Ala Asn Phe Gly Pro Arg Lys Arg Arg Arg
1               5                   10                  15

Arg Arg Arg

<210> SEQ ID NO 12
<211> LENGTH: 16
<212> TYPE: PRT
<213> ORGANISM: Artificial sequence
<220> FEATURE:
<223> OTHER INFORMATION: Synthetic peptide

<400> SEQUENCE: 12

Arg Arg Arg Lys Arg Asn Arg Asp Ala Arg Arg Arg Arg Lys Gln
1               5                   10                  15

<210> SEQ ID NO 13
<211> LENGTH: 17
<212> TYPE: PRT
<213> ORGANISM: Artificial sequence
<220> FEATURE:
<223> OTHER INFORMATION: Synthetic peptide

<400> SEQUENCE: 13

Met Gln Arg Lys Pro Thr Ile Arg Arg Lys Asn Leu Arg Leu Arg Arg
1               5                   10                  15

Lys

<210> SEQ ID NO 14
<211> LENGTH: 7
<212> TYPE: PRT
<213> ORGANISM: Artificial sequence
<220> FEATURE:
<223> OTHER INFORMATION: Synthetic peptide

<400> SEQUENCE: 14

Ile Met Arg Arg Arg Gly Leu
1               5

<210> SEQ ID NO 15
<211> LENGTH: 8
<212> TYPE: PRT
<213> ORGANISM: Artificial sequence
<220> FEATURE:
<223> OTHER INFORMATION: Synthetic peptide

<400> SEQUENCE: 15

Lys Lys Leu Lys Lys Arg Asn Lys
1               5

<210> SEQ ID NO 16
<211> LENGTH: 9
<212> TYPE: PRT
<213> ORGANISM: Artificial sequence
<220> FEATURE:
<223> OTHER INFORMATION: Synthetic peptide

<400> SEQUENCE: 16

Arg Arg Arg Ala Asn Asn Arg Arg Arg
1               5

<210> SEQ ID NO 17
<211> LENGTH: 7
<212> TYPE: PRT
<213> ORGANISM: Artificial sequence
<220> FEATURE:
<223> OTHER INFORMATION: Synthetic peptide

<400> SEQUENCE: 17

```
Arg Lys Lys Arg Lys Lys Lys
1               5

<210> SEQ ID NO 18
<211> LENGTH: 15
<212> TYPE: PRT
<213> ORGANISM: Artificial sequence
<220> FEATURE:
<223> OTHER INFORMATION: Synthetic peptide

<400> SEQUENCE: 18

Lys Arg Lys Gly Lys Leu Lys Asn Lys Gly Ser Lys Arg Lys Lys
1               5                   10                  15

<210> SEQ ID NO 19
<211> LENGTH: 18
<212> TYPE: PRT
<213> ORGANISM: Artificial sequence
<220> FEATURE:
<223> OTHER INFORMATION: Synthetic peptide

<400> SEQUENCE: 19

Ser Lys Arg Leu Ser Ser Arg Ala Arg Lys Arg Ala Ala Lys Arg Arg
1               5                   10                  15

Leu Gly

<210> SEQ ID NO 20
<211> LENGTH: 14
<212> TYPE: PRT
<213> ORGANISM: Artificial sequence
<220> FEATURE:
<223> OTHER INFORMATION: Synthetic peptide

<400> SEQUENCE: 20

Lys Arg Pro Arg Arg Arg Pro Ser Arg Pro Phe Arg Lys Pro
1               5                   10

<210> SEQ ID NO 21
<211> LENGTH: 13
<212> TYPE: PRT
<213> ORGANISM: Artificial sequence
<220> FEATURE:
<223> OTHER INFORMATION: Synthetic peptide

<400> SEQUENCE: 21

Lys Lys Arg Thr Leu Arg Lys Asn Asp Arg Lys Lys Arg
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide

<400> SEQUENCE: 22

Trp Arg Arg Gln Ala Arg Phe Lys
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 23

Arg Lys Lys Arg Arg Gln Arg Arg Arg
1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic peptide

<400> SEQUENCE: 24

Tyr Ala Arg Ala Ala Ala Arg Gln Ala Arg Ala
1               5                   10

<210> SEQ ID NO 25
<211> LENGTH: 18
<212> TYPE: PRT
<213> ORGANISM: Artificial Sequence
<220> FEATURE:
<223> OTHER INFORMATION: Synthetic peptide

<400> SEQUENCE: 25

Lys Gly Arg Gln Val Lys Val Trp Phe Gln Asn Arg Arg Met Lys Trp
1               5                   10                  15

Lys Lys

<210> SEQ ID NO 26
<211> LENGTH: 29
<212> TYPE: PRT
<213> ORGANISM: Artificial Sequence
<220> FEATURE:
<223> OTHER INFORMATION: Synthetic peptide

<400> SEQUENCE: 26

Met Leu Ser Tyr Leu Ile Phe Ala Leu Ala Val Ser Pro Ile Leu Gly
1               5                   10                  15

Lys Lys Arg Thr Leu Arg Lys Asn Asp Arg Lys Lys Arg
            20                  25

<210> SEQ ID NO 27
<211> LENGTH: 29
<212> TYPE: PRT
<213> ORGANISM: Artificial Sequence
<220> FEATURE:
<223> OTHER INFORMATION: Synthetic peptide

<400> SEQUENCE: 27

Met Lys Thr Ile Ile Ala Leu Ser Tyr Ile Phe Cys Leu Ala Leu Gly
1               5                   10                  15

Lys Lys Arg Thr Leu Arg Lys Asn Asp Arg Lys Lys Arg
            20                  25

<210> SEQ ID NO 28
<211> LENGTH: 28
<212> TYPE: PRT
<213> ORGANISM: Artificial Sequence
<220> FEATURE:
<223> OTHER INFORMATION: Synthetic peptide
```

```
<400> SEQUENCE: 28

Met Lys Ala Ile Ile Val Leu Leu Met Val Val Thr Ser Asn Ala Lys
1               5                   10                  15

Lys Arg Thr Leu Arg Lys Asn Asp Arg Lys Lys Arg
            20                  25
```

ANTIVIRAL PEPTIDE AND USE THEREFOR

BACKGROUND OF THE INVENTION

1. Field of the Invention

The present invention relates to an artificially synthesized antiviral peptide having antiviral activity against at least one kind of virus, and to a use therefor. It relates particularly to the use of an artificial peptide comprising an amino acid sequence (hereunder also called a "signal sequence") constituting a signal peptide of several virus species, together with a cell penetrating peptide sequence.

The priority claim for this application is based on Japanese Patent Application No. 2017-193292 filed on Oct. 3, 2017, and the entire contents of that application are herein incorporated by reference.

2. Description of the Related Art

The vesicular stomatitis virus (VSV) is a virus belonging to Vesiculovirus genus in Rhabdoviridae family of RNA viruses, and is a pathogenic virus that causes vesicular stomatitis, which is an infectious disease of livestock. Therefore, VSV is a virus of great interest for disease prevention in livestock. Meanwhile, research using VSV as a viral vector has become active in recent years, and the virus has gained attention as a tool for expressing desired proteins in target cells, and for introducing specific genes into target cells. WO 2009/019612 may be consulted for example.

There are presently only a limited number of drugs (antiviral agents) that are effective for preventing or treating viral diseases of humans or non-human mammals, and development of new antiviral drugs is being actively pursued from a number of approaches. One approach that is being tried is the development of naturally derived or artificially prepared antiviral peptides capable of inhibiting or reducing the growth of viruses. WO 2011/151341, Japanese Patent Application Publication No. 2007-230904 and Japanese Patent Application Publication No. 2007-230903 may be consulted for example.

SUMMARY OF THE INVENTION

It is an object of the present invention to design a peptide with a different structure from the antiviral peptides described in WO 2009/019612, WO 2011/151341, Japanese Patent Application Publication No. 2007-230904, and Japanese Patent Application Publication No. 2007-230903, which is a novel artificial antiviral peptide differing from peptides that exist and function as antiviral peptides in nature. Other objects are to manufacture the antiviral peptide designed in this invention, and to provide an antiviral composition having this peptide as a principal component (typically, a pharmaceutical composition as an antiviral agent or research reagent).

The inventors focused on the amino acid sequence of a glycoprotein encoded for by the VSV G gene (hereunder also called a "VSV-G glycoprotein"). Surprisingly, we discovered that a synthetic peptide obtained by combining the signal sequence of this VSV-G glycoprotein with a conventionally known amino acid sequence (hereunder also called a "CPP sequence") that functions as a cell penetrating peptide (CPP) has excellent antiviral activity against at least one kind of virus (typically, the activity of inhibiting the growth of at least one kind of virus).

After expanding our research to include other virus species, we perfected the present invention after discovering that a synthetic peptide obtained by combining a CPP sequence with the signal sequence of hemagglutinin encoded for by the HA gene of the influenza A virus or influenza B virus in the Orthomyxoviridae family of RNA viruses has similar antiviral activity.

That is, the synthetic peptide disclosed here is an antiviral peptide having antiviral activity against at least one kind of virus.

This peptide comprises the amino acid sequences shown in (1) and (2) below:

(1) a signal sequence of a glycoprotein (VSV-G glycoprotein) encoded for by the G gene of the vesicular stomatitis virus (VSV), or a signal sequence of hemagglutinin encoded for by the HA gene of the influenza A or influenza B virus, or a modified amino acid sequence formed by conservative substitution of 1, 2 or 3 amino acid residues in any of these signal sequences; and (2) an amino acid sequence that functions as a cell penetrating peptide (CPP).

In a preferred embodiment, the total number of amino acid residues in the antiviral peptide disclosed here is not more than 100. From the standpoint of manufacturing costs, ease of synthesis and handling properties, the total number of amino acid residues is more preferably not more than 50 (such as not more than 30).

Alternatively, a synthetic peptide in which the combined number of amino acid residues in the amino acid sequence of (1) and the amino acid sequence of (2) above constitutes at least 80% (more preferably at least 90%, such as 100%) of the amino acid residues in the antiviral peptide as a whole is an especially preferred embodiment of the antiviral peptide disclosed here.

In another preferred embodiment of the antiviral peptide disclosed here, the signal sequence of (1) above is an amino acid sequence represented by any of SEQ ID NOS: 1 to 7.

In another preferred embodiment of the antiviral peptide disclosed here, moreover, the amino acid sequence of (2) above that functions as a CPP is a polyarginine (typically composed of 5 to 9 arginine residues, although the number is not particularly limited), an amino acid sequence represented by any of SEQ ID NOS: 8 to 25, or a modified amino acid sequence formed by conservative substitution of 1, 2 or 3 amino acid residues in this amino acid sequence.

The present invention also provides an antiviral composition for inhibiting the growth of at least one kind of virus, comprising any of the synthetic peptides (antiviral peptides) disclosed here together with at least one kind of pharmacologically acceptable carrier.

Because it contains the antiviral peptide disclosed here, this composition can be used as an antiviral agent, or as a research material for developing new antiviral agents.

The present invention also provides a method for inhibiting the growth of at least one kind of virus, wherein any of the synthetic peptides (antiviral peptides) disclosed here is supplied at least once to a target cell, tissue or the like (either in vitro or in vivo, for example).

With a method of this configuration, the growth of at least one kind of virus (such as VSV) can be arrested or inhibited by supplying the antiviral peptide disclosed here to a target.

DESCRIPTION OF THE PREFERRED EMBODIMENTS

Preferred embodiments of the present invention are explained below. Matters other than those specifically mentioned in this Description (such as the primary structure and chain length of the synthetic peptide disclosed here) that are necessary for implementing the present invention (such as methods for chemical synthesis of peptides, cell culture methods, and ordinary matters relating to preparation of an antiviral composition having the peptide disclosed here as a component) can be understood as design matters by a person skilled in the art based on prior art in the fields of cell engineering, physiology, medicine, pharmacology, organic chemistry, biochemistry, genetic engineering, protein engineering, molecular biology, genetics and the like. The present invention can be implemented based on the content disclosed in this Description and on technical common knowledge in these fields. In the explanations below, amino acids are represented by 1-letter notation (but by 3-letter notation in the sequence tables).

The entire contents of all literature cited in this Description are incorporated by reference in this Description.

In this Description, an "artificially synthesized peptide" is not a peptide whose peptide chain exists stably and independently by itself in nature, but rather a peptide fragment that has been manufactured by artificial chemical synthesis or biosynthesis (that is, production based on genetic engineering), and that can exist stably in a specific system (for example, a composition constituting an antiviral agent). The term "peptide" here refers to an amino acid polymer having multiple peptide bonds, and while the number of amino acid residues in the peptide chain is not particularly limited, it typically refers to those with relatively low molecular weights comprising not more than about 100 (preferably not more than 80, or more preferably not more than 70, or especially not more than 50, such as not more than 30) total amino acid residues.

Unless otherwise specified, in this Description the term "amino acid residue" encompasses the N-terminal amino acid and C-terminal amino acid of the peptide chain.

The amino acid sequences described in this Description are always N-terminal on the left side and C-terminal on the right.

In this Description, a "modified amino acid sequence" relative to a given amino acid sequence is an amino acid sequence formed by substituting, deleting or adding (inserting) 1 or more (typically not more than 9, or preferably not more than 5) amino acid residues, such as 1, 2 or 3 amino acid residues, without losing the original function (such as antiviral activity or cell membrane penetrating ability) of the given amino acid sequence. Typical examples of modified amino acid sequences in this Description include sequences formed by so-called conservative amino acid replacement of 1, 2 or 3 amino acid residues (for example, sequences having basic amino acid residues substituted for other basic amino acid residues, such as mutual substitution of lysine and arginine residues), and sequences obtained by adding (inserting) or deleting 1, 2 or 3 amino acid residues in a given amino acid sequence.

Thus, specific examples of the antiviral peptide disclosed here include not only synthetic peptides comprising amino acid sequences identical to the amino acid sequences of the sequence ID numbers described below, but also synthetic peptides comprising modified amino acid sequences formed by substituting (typically by conservative substitution), deleting or adding 1, 2 or 3 amino acid residues in the amino acid sequences of the sequence ID numbers, and exhibiting antiviral activity equivalent to that of the amino acid sequences of these sequence ID numbers.

The artificially synthesized antiviral peptide disclosed here is a short-chain peptide that does not exist in nature, comprising the two kinds of amino acid sequences described above, namely:

(1) the signal sequence of the VSV-G glycoprotein, or the signal sequence of hemagglutinin encoded for by the HA gene of the influenza A or influenza B virus, or a modified amino acid sequence formed by conservative substitution of 1, 2 or 3 amino acid residues in any of these signal sequences; and (2) an amino acid sequence that functions as a CPP.

The VSV-G glycoprotein is a transmembrane type I glycoprotein, and is currently used as a glycoprotein constituting the envelope of "retrovirus vectors". However, the signal peptide region of the VSV-G glycoprotein was not previously found to have antiviral activity, and the idea that an artificially synthesized antiviral peptide could be obtained by synthesizing the amino acid sequence of this signal peptide region and adding a CPP thereto was not imagined at the time of filing of this application.

Similarly, although the hemagglutinin encoded for by the HA genes of the influenza A and influenza B viruses is well known as a glycoprotein present on the surface of viral particles that plays an important role in the infection of host cells, the signal peptide region of this hemagglutinin was not previously found to have antiviral activity, and the idea that an artificially synthesized antiviral peptide could be obtained by synthesizing the amino acid sequence of this signal peptide region and adding a CPP thereto was not imagined at the time of filing of this application.

Amino acid sequence data about the VSV-G glycoprotein and the hemagglutinin of the influenza A and influenza B viruses can be easily obtained by accessing the databases of various known international organization. For example, data about the total amino acid sequences of these glycoproteins and the amino acid sequences of their signal peptide regions is recorded in the data base (UniProtKB) of the Universal Protein Resource (UniProt), and can be easily obtained by anyone.

Desirable examples of the signal sequences of the VSV-G glycoprotein and hemagglutinin include, but are not particularly limited to, the sequences of SEQ ID NOS: 1 to 7. Specifically, these are as follows.

SEQ ID NO: 1 (UniProtKB-P04882) is a signal sequence of 16 amino acid residues contained in the VSV-G glycoprotein of one kind of isolated VSV (vesicular stomatitis New Jersey virus).

SEQ ID NO: 2 (UniProtKB-P03437) is a signal sequence of 16 amino acid residues contained in the hemagglutinin of one kind of isolated influenza A virus.

SEQ ID NO: 3 (UniProtKB-P03460) is a signal sequence of 15 amino acid residues contained in the hemagglutinin of one kind of isolated influenza B virus.

SEQ ID NO: 4 (UniProtKB-P04884) is a signal sequence of 16 amino acid residues contained in the VSV-G glycoprotein of one kind of isolated VSV (vesicular stomatitis Indiana virus).

SEQ ID NO: 5 (UniProtKB-P03440) is a signal sequence of 16 amino acid residues contained in the hemagglutinin of one kind of isolated influenza A virus.

SEQ ID NO: 6 (UniProtKB-P03435) is a signal sequence of 16 amino acid residues contained in the hemagglutinin of one kind of isolated influenza A virus.

SEQ ID NO: 7 (UniProtKB-P03439) is a signal sequence of 16 amino acid residues contained in the hemagglutinin of one kind of isolated influenza A virus.

Various conventionally known CPPs can be used as the amino acid sequence that functions as a CPP for constructing the antiviral peptide disclosed here. For example, so-called polyarginine (Rn) consisting of at least 3, or preferably at least 5 and not more than 11, or preferably not more than 9 arginine residues can be used favorably as the CPP here. Various other known CPPs may also be used.

Desirable examples include, but are not limited to, the CPPs of SEQ ID NOS: 8 to 25. Specifically, these are as follows.

The amino acid sequence of SEQ ID NO: 8 corresponds to a nucleolar localization signal (NoLS) comprising a total of 14 amino acid residues derived from basic fibroblast growth factor (FGF2).

The amino acid sequence of SEQ ID NO: 9 corresponds to a NoLS comprising a total of 19 amino acid residues derived from one kind of nucleolar protein (ApLLP).

The amino acid sequence of SEQ ID NO: 10 corresponds to a NoLS comprising a total of 16 amino acid residues derived from a protein (γ(1)34.5) of herpes simplex virus type I (HSV-1).

The amino acid sequence of SEQ ID NO: 11 corresponds to a NoLS comprising a total of 19 amino acid residues derived from human I-mfa domain-containing protein (HIC) p40 protein.

The amino acid sequence of SEQ ID NO: 12 corresponds to a NoLS comprising a total of 16 amino acid residues derived from the MEQ protein of Marek's disease virus (MDV).

The amino acid sequence of SEQ ID NO: 13 corresponds to a NoLS comprising a total of 17 amino acid residues derived from survivin-deltaEx3, a protein that inhibits apoptosis.

The amino acid sequence of SEQ ID NO: 14 corresponds to a NoLS comprising a total of 7 amino acid residues derived from the vascular growth factor angiogenin.

The amino acid sequence of SEQ ID NO: 15 corresponds to a NoLS comprising a total of 8 amino acid residues derived from MDM2, a nuclear protein that forms a composite with the p53 tumor suppressor protein.

The amino acid sequence of SEQ ID NO: 16 corresponds to a NoLS comprising a total of 9 amino acid residues derived from GGNNVα, a betanoda virus protein.

The amino acid sequence of SEQ ID NO: 17 corresponds to a NoLS comprising a total of 7 amino acid residues derived from NF-κB-inducing kinase (NIK).

The amino acid sequence of SEQ ID NO: 18 corresponds to a NoLS comprising a total of 15 amino acid residues from nuclear VCP-like protein.

The amino acid sequence of SEQ ID NO: 19 corresponds to a NoLS comprising a total of 18 amino acid residues derived from the nucleolar protein p120.

The amino acid sequence of SEQ ID NO: 20 corresponds to a NoLS comprising a total of 14 amino acid residues derived from the ORF57 protein of herpes virus saimiri (HVS).

The amino acid sequence of SEQ ID NO: 21 corresponds to a NoLS comprising a total of 13 amino acid residues extending from the No. 491 amino acid residue to the No. 503 amino acid residue of LIM kinase 2, a protein kinase involved in intracellular signal transduction that is present in human endothelial cells.

The amino acid sequence of SEQ ID NO: 22 corresponds to a NoLS comprising a total of 8 amino acid residues contained in a nucleocapsid protein (N protein) of avian infectious bronchitis virus (IBV).

The amino acid sequence of SEQ ID NO: 23 corresponds to a membrane-permeable motif comprising a total of 9 amino acid sequences derived from a protein transduction domain contained in the TAT of human immunodeficiency virus (HIV).

The amino acid sequence of SEQ ID NO: 24 corresponds to a membrane-permeable motif comprising a total of 11 amino acid sequences of a modified protein transduction domain (PTD4) of the same TAT.

The amino acid sequence of SEQ ID NO: 25 corresponds to a membrane-permeable motif comprising a total of 18 amino acid sequences derived from the ANT of Antennapedia, a mutant form of *Drosophila*.

Of these, the amino acid sequences (or modified amino acid sequences thereof) associated with NoLS and TAT are particularly desirable. For example, a NoLS-associated CPP sequence such as those of SEQ ID NO: 21 or 22 or the TAT- and ANT-associated CPP sequences of SEQ ID NOS: 23 to 25 can be used favorably to construct the antiviral peptide disclosed here.

As long as the peptide chain (amino acid sequence) of the antiviral peptide disclosed here is provided with the amino acid sequence of (1) above (hereunder generally called the "(1) antiviral signal sequence") and the amino acid sequence of (2) above (hereunder generally called the "(2) CPP sequence"), either the (1) antiviral signal sequence or the (2) CPP sequence may be disposed on the N-terminal side (C-terminal side) of the chain relative to the other.

Preferably the (1) antiviral signal sequence and (2) CPP sequence are substantially adjacent to one another. Specifically, preferably either no amino acid residues not belonging to either sequence are disposed between the (1) antiviral signal sequence and the (2) CPP sequence, or when present, the number of such amino acid residues is preferably not more than about 10 (more preferably not more than 5, such as 1 or 2 amino acid residues).

As long as the antiviral activity of inhibiting the growth of at least one kind of virus is not impaired, it is also possible to include a sequence (amino acid residue) part other than the amino acid sequences of the (1) antiviral signal sequence and (2) CPP sequence.

In the antiviral peptide disclosed here, the total number of amino acid residues constituting the peptide chain is suitably not more than 100, or preferably not more than 80, or more preferably not more than 70 (such as a peptide chain of 30 to 50 amino acid residues). A peptide with such a short chain length is easy to chemically synthesize, so the antiviral peptide can be provided easily. The shape of the peptide is not particularly limited, but a linear or helical peptide is preferred because it is unlikely to become an immunogen (antigen). Peptides with such shapes are unlikely to constitute epitopes.

The combined number of amino acid residues in the (1) antiviral signal sequence and (2) CPP sequence as a percentage of the total number of amino acid residues in the synthesized peptide as a whole is not particularly limited as long as antiviral activity is retained, but is preferably at least about 80%, or more preferably at least 90%. Preferably all of the amino acid residues are L-amino acids, but D-amino acids may be substituted for part or all of the amino acid residues as long as antiviral activity is not impaired.

Preferably at least one amino acid residue is amidated in the antiviral peptide disclosed here. The structural stability (such as protease resistance) of the synthetic peptide can be improved by amidating a carboxyl group of an amino acid residue (typically, the C-terminal amino acid residue of the peptide chain).

The antiviral peptide disclosed here can be easily manufactured by ordinary chemical synthesis methods. For example, either a conventional known solid-phase synthesis method or liquid-phase synthesis method may be used. A solid-phase synthesis method using t-butyloxycarbonyl (Boc) or 9-fluorenylmethoxycarbonyl (Fmoc) as the amino-protecting group is preferred.

For the antiviral peptide disclosed here, a peptide chain having the desired amino acid sequences and modified (C-terminal amidated, etc.) parts can be synthesized by solid-phase synthesis using a commercial peptide synthesizer.

Alternatively, the antiviral peptide of the invention may be biosynthesized by genetic engineering methods. That is, a polynucleotide (typically DNA) is synthesized with a nucleotide sequence (including ATG initiation codon) encoding for the amino acid sequence of a desired antiviral peptide. A recombinant vector having a gene expression cassette comprising the synthesized polynucleotide (DNA) together with various regulatory elements (including promoters, ribosome binding sites, terminators, enhancers, and various cis-elements for controlling expression level) for causing expression of the amino acid sequence in host cells can then be constructed according to the host cells.

This recombinant vector is then introduced into specific host cells (such as yeast, insect or plant cells) by ordinary methods, and the host cells or a tissue or individual organism containing those cells is cultured under specific conditions. The target peptide can thus be expressed and produced in cells. The peptide can then be isolated from the host cells (or from medium when it has been excreted), and refolded, purified or the like as necessary to obtain the target antiviral peptide.

Methods conventionally used in the field can be adopted as the methods for constructing a recombinant vector and introducing the constructed recombinant vector into host cells and the like, and detailed explanations are omitted because these methods themselves are not a particular feature of the present invention.

Alternatively, template DNA (that is, a synthetic gene fragment containing a nucleotide sequence encoding for the amino acid sequence of the antiviral peptide) for use in a cell-free protein synthesis system can be constructed, and a target polypeptide can be synthesized in vitro with a so-called cell-free protein synthesis system using various compounds necessary for peptide synthesis (ATP, RNA polymerase, amino acids, etc.). The papers of Shimizu et al. (Shimizu et al., Nature Biotechnology, 19, 751-755 (2001)) and Madin et al. (Madin et al., Proc. Natl. Acad. Sci. USA, 97(2), 559-564 (2000)) for example may be consulted regarding cell-free protein synthesis systems. Based on the techniques described in these papers, many companies have already commissioned polypeptide products at the time of filing of this application, and cell-free protein synthesis kits (available from CellFree Sciences Co., Ltd. in Japan for example) are marketed.

A single- or double-stranded polynucleotide comprising a nucleotide sequence encoding for the antiviral peptide disclosed here and/or a nucleotide sequence complementary to that sequence can be easily manufactured (synthesized) by conventional known methods. That is, a nucleotide sequence corresponding to the amino acid sequence of the antiviral peptide can be easily determined and provided by selecting codons corresponding to each amino acid residue constituting the designed amino acid sequence. Once the nucleotide sequence has been determined, a (single-stranded) polynucleotide corresponding to the desired nucleotide sequence can then be easily obtained with a DNA synthesizer or the like. Furthermore, the resulting single-stranded DNA can then be used as a template to obtain a target double-stranded DNA by various enzymatic synthesis techniques (typically PCR). The polynucleotide may be in the form of either DNA or RNA (mRNA or the like). The DNA may be provided in either double-stranded or single-stranded form. In the case of single-stranded DNA, it may be either a coding strand (sense strand) or a non-coding strand (antisense strand) complementary to the sense strand.

As discussed above, the resulting polynucleotide can be used in various host cells and cell-free protein synthesis systems as a material for constructing a recombinant gene (expression cassette) for producing the antiviral peptide.

The antiviral peptide disclosed here has strong antiviral activity against at least one kind of virus. For example, it may display strong antiviral activity against a virus whose genome is single-stranded RNA, such as VSV or another virus in the Rhabdoviridae family. For example, it can be used to treat or prevent infection by this kind of virus, such as in a mouthwash (gargle), eyewash or the like.

When the antiviral peptide is contained in an antiviral composition (antiviral agent), it may be in the form of a salt as long as its antiviral activity is not impaired. For example, it is possible to use an acid-addition salt of the peptide obtained by an addition reaction performed by ordinary methods with a commonly used inorganic or organic acid. Other salts (such as metal salts) are also possible. Thus, the "peptide" described in this Description and in the Claims encompasses peptide salts.

The antiviral composition disclosed here may contain various pharmacologically (pharmaceutically) acceptable carriers according to the usage form as long as antiviral activity of the antiviral peptide, which is the active ingredient of the composition, is retained. For example, carriers commonly used as diluents, excipients and the like in peptide medicines may be used.

The type of carrier differs according to the usage and form of the antiviral composition disclosed here, but typical examples include water, physiological buffer solutions, and various organic solvents. Other examples include aqueous solutions of alcohols (such as ethanol) at suitable concentrations, glycerol, and non-drying oils such as olive oil, as well as liposomes. Examples of accessory components that may be included in the antiviral composition include various fillers, bulking agents, binders, humectants, surfactants, dyes, perfumes and the like.

Typical forms of the antiviral composition (antiviral agent) include liquids, suspensions, emulsions, aerosols, foams, granules, powders, pills, capsules, ointments, aqueous gels and the like. The composition may also be in the form of a freeze-dried composition or granules that are dissolved in saline or a suitable buffer (such as PBS) before use to prepare a liquid for injection.

The processes for preparing compositions (medicines) in various forms using the antiviral peptide (principal component) and various carriers (accessory components) may be based on conventional known methods, and detailed explanations are omitted because such preparation methods are not themselves a feature of the present invention. Sources of detailed information about formulations include Comprehensive Medicinal Chemistry, Corwin Hansch Ed., Pergamon Press (1990). The entire contents of this text are incorporated by reference in this Description.

The antiviral composition (antiviral agent) disclosed here may be used by a method and at a dosage suited to the form and purpose thereof.

The antiviral peptide disclosed here can maintain its antiviral activity even in systems containing relatively high concentrations of cations or salts (such as sodium chloride), or organic matter such as serum for example. Consequently, the antiviral composition disclosed here is desirable for use in systems (locations) where cations, salts, serum or the like are present. For example, the antiviral composition provided by the present invention can be administered to a patient as a liquid agent by intravenous, intramuscular, subcutaneous, intradermal or intraperitoneal injection, or by irrigation.

It can also be administered orally in a solid form such as a pill or the like. When used for cleaning the surfaces of sanitary ware, a liquid agent containing a relatively large quantity (such as 1 to 100 mg/mL) of the antiviral peptide can be sprayed directly on a target surface, or this liquid agent can be wiped on a target surface with a wet cloth or paper. These are only examples, and the peptide may be applied in the same forms and by the same methods as conventional peptide antibiotics and pesticides and quasi-drugs containing peptides as active ingredients.

A polynucleotide coding for the antiviral peptide can be used as a material for so-called gene therapy. For example, a gene encoding for the antiviral peptide (typically a DNA segment or RNA segment) can be incorporated into a suitable vector, and introduced into a target site to thereby cause constant expression of the antiviral peptide of the invention in a living body (cells). Consequently, a polynucleotide (DNA segment, RNA segment, etc.) encoding for the antiviral peptide of the invention is useful as a medicine for preventing or treating viral infection.

In the field of regenerative medicine, it is important to prevent viral infection when culturing skin, bone and various organs. The antiviral peptide disclosed here exhibits very little toxicity towards mammalian cells and tissues, and has a selective antiviral effect against at least one kind of virus. Consequently, it is highly useful as a medicine for preventing viral infection of cultured organs and the like. For example, as shown in the examples below, viral infection of organs, tissues, cells and the like in culture can be prevented, or viral growth in a host can be inhibited, by including the antiviral peptide disclosed here at a suitable concentration in the culture solution.

Some examples of the present invention are explained in detail below, but the intent is not to limit the present invention to what is shown in these examples.

TABLE 1

| Sample No. | Amino acid sequence | Total amino acid residues |
|---|---|---|
| 1 | MLSYLIFALAVSPILGKKRTLRKNDRKKR-$CONH_2$ (SEQ ID NO: 26) | 29 |
| 2 | MKTIIALSYIFCLALGKKRTLRKNDRKKR-$CONH_2$ (SEQ ID NO: 27) | 29 |
| 3 | MKAIIVLLMVVTSNAKKRTLRKNDRKKR-$CONH_2$ (SEQ ID NO: 28) | 28 |

Test Example 1: Peptide Synthesis and Preparation of Peptide-Containing Medium

The three peptides shown in Table 1 were manufactured with a commercial peptide synthesizer. The specifics are as follows.

Sample 1 is a synthetic peptide comprising the amino acid sequence of SEQ ID NO: 1 (VSV-G glycoprotein signal sequence) as the (1) antiviral signal sequence, together with the amino acid sequence of SEQ ID NO: 21 (LIM kinase 2 NoLS) as the (2) CPP sequence on the C-terminal side of the sequence (1).

Sample 2 is a synthetic peptide comprising the amino acid sequence of SEQ ID NO: 2 (influenza A virus hemagglutinin signal sequence) as the (1) antiviral signal sequence, together with the amino acid sequence of SEQ ID NO: 21 (LIM kinase 2 NoLS) as the (2) CPP sequence on the C-terminal side of the sequence (1).

Sample 3 is a synthetic peptide comprising the amino acid sequence of SEQ ID NO: 3 (influenza B virus hemagglutinin signal sequence) as the (1) antiviral signal sequence, together with the amino acid sequence of SEQ ID NO: 21 (LIM kinase 2 NoLS) as the (2) CPP sequence on the C-terminal side of the sequence (1).

The peptides of these samples 1 to 3 were all synthesized by solid-phase synthesis (Fmoc method) using a commercial peptide synthesizer according to the manual. The mode of use of the peptide synthesizer is not explained in detail because it is not a feature of the invention. In all the synthesized peptides, the carboxyl group (—COOH) of the C-terminal amino acid is amidated (—$CONH_2$).

The synthesized peptides of each sample were dissolved in dimethyl sulfoxide (DMSO) to prepare stock solutions (concentration 2.5 mM) of each sample peptide.

Next, a suitable amount of the stock solution of any of the above sample peptides was supplied to Eagle's minimum essential medium (MEM) containing 0.3% bovine serum albumin (BSA), 100 U/mL penicillin and 0.1 mg/mL streptomycin, to prepare a test peptide-containing MEM containing any of the synthetic peptides at a concentration of 10 μM or 50 μM. Control MEM containing none of the sample peptides was also prepared as a control.

Test Example 2: Test to Evaluate Antiviral Activity of Each Synthetic Peptide

The antiviral activity (viral growth inhibitory effect) of the synthetic peptide of each sample was investigated. In this test example, titer (infectivity) was measured based on the TCID50 method using the vesicular stomatitis Indiana virus (Indiana VSV) as the target virus. The specifics are as follows.

First, the previously-obtained test virus (Indiana VSV) was diluted appropriately to prepare a virus solution having an infectivity value of $10^3$ $TCID_{50}$/mL.

MDCK cells (canine kidney epithelial cells) were cultured in advance on a commercial 6-well plate, and each culture well was inoculated with 1 mL of the virus solution with the aforementioned infectivity. This was incubated at 37° C. for about 1 hour after inoculation, after which the virus solution was removed from each well, and each well was washed once with PBS.

Next, 2 mL of any of the test peptide-containing MEMs prepared above or the control MEM was supplied per well, and cultured at 35° C.

24 hours after the start of culture, the supernatant was collected from each well, and a known general plaque assay was performed using MDCK cells not infected with a virus. The results are shown in Table 2. In Table 2, the virus infectivity (virus titer) is shown in units of $\log_{10}$ PFU/mL. The lower this number, the lower the virus infectivity.

TABLE 2

| | Virus infectivity ($\log_{10}$ PFU/mL) | |
|---|---|---|
| | Provided peptide concentration | |
| Test sample No. | 10 μM | 50 μM |
| No. 1 | 9.11 | 5.90 |
| No. 2 | 9.07 | 5.95 |
| No. 3 | 9.23 | 6.34 |
| Control | | 9.04 |

As shown by the logarithmic values for virus infectivity in Table 2, all of the peptides of samples 1 to 3 exhibited good antiviral activity (virus growth inhibition effects) against the test VSV as a result of an assay at a peptide concentration of 50 μM.

These results confirm that the antiviral peptide disclosed here can exhibit antiviral activity against at least one kind of target virus. No cytotoxicity was observed with any of the sample peptides.

Specific examples of the present invention were explained in detail here, but these are only examples and do not limit the scope of the Claims. The technology described in the claims encompasses various changes and modifications to the specific examples described above.

For example, the sequences of SEQ ID NOS: 1 to 3 are used as the (1) antiviral signal sequence in the examples, but another known (1) antiviral signal sequence (such as those of SEQ ID NOS: 4 to 7) or a modified sequence thereof may be used. Moreover, the sequence of SEQ ID NO: 21 is used as the (2) CPP sequence in the examples, but another known (2) CPP sequence (such as those of SEQ ID NOS: 8 to 20 and 22 to 25) may also be used.

As discussed above, the growth of at least one kind of virus can be suppressed (or viral infection can be prevented) with the antiviral peptide disclosed here. Consequently, by using the antiviral peptide provided by the present invention, it is possible to provide an antiviral composition (antiviral agent) that inhibits the growth of at least one kind of virus.

What is claimed is:

1. A synthetic peptide that suppresses growth of VSV, the synthetic peptide comprising amino acid sequences shown in (1) and (2) below:
    (1) an amino acid sequence represented by any one of SEQ ID NOS: 1 to 7; and
    (2) an amino acid sequence represented by any one of SEQ ID NOS: 8 to 25.

2. The synthetic peptide according to claim 1, wherein the total number of amino acid residues is not more than 100.

3. The synthetic peptide according to claim 1, having an amino acid sequence represented by any one of SEQ ID NOS: 26 to 28.

4. An antiviral composition that suppresses growth of VSV, the antiviral composition comprising:
    the synthetic peptide according to claim 1; and
    at least one kind of pharmacologically acceptable carrier.

5. A method for suppressing growth of VSV, the method comprising supplying the synthetic peptide according to claim 1 at least once to a target in vitro.

* * * * *

UNITED STATES PATENT AND TRADEMARK OFFICE
CERTIFICATE OF CORRECTION

PATENT NO. : 10,745,448 B2  
APPLICATION NO. : 16/149435  
DATED : August 18, 2020  
INVENTOR(S) : Yoshida et al.

Page 1 of 1

It is certified that error appears in the above-identified patent and that said Letters Patent is hereby corrected as shown below:

On the Title Page

Item (73), should read as follows:  
Toagosei Co, LTD, Tokyo (JP)  
National University Corporation Hokkaido University, Hokkaido (JP)

Signed and Sealed this  
Thirty-first Day of August, 2021

Drew Hirshfeld  
*Performing the Functions and Duties of the*  
*Under Secretary of Commerce for Intellectual Property and*  
*Director of the United States Patent and Trademark Office*